United States Patent
Takagi

(10) Patent No.: US 9,514,529 B2
(45) Date of Patent: Dec. 6, 2016

(54) DIAGNOSTIC READING REQUEST SYSTEM, DIAGNOSTIC READING REQUEST INTERMEDIARY DEVICE, CONTROL PROGRAM, AND DIAGNOSTIC READING RESULT EVALUATION METHOD

(71) Applicant: Shingo Takagi, Otawara (JP)

(72) Inventor: Shingo Takagi, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 672 days.

(21) Appl. No.: 13/713,107

(22) Filed: Dec. 13, 2012

(65) Prior Publication Data
US 2013/0136330 A1    May 30, 2013

Related U.S. Application Data

(63) Continuation of application No. PCT/JP2011/073226, filed on Oct. 7, 2011.

(51) Int. Cl.
G06T 7/00    (2006.01)
A61B 6/00    (2006.01)
G06F 19/00    (2011.01)

(52) U.S. Cl.
CPC ............ *G06T 7/0012* (2013.01); *A61B 6/563* (2013.01); *G06F 19/321* (2013.01); *G06F 19/327* (2013.01); *G06F 19/328* (2013.01); *G06F 19/3418* (2013.01)

(58) Field of Classification Search
None
See application file for complete search history.

(56) References Cited

U.S. PATENT DOCUMENTS

2004/0081342 A1    4/2004    Sato
2006/0052676 A1    3/2006    Wang et al.
(Continued)

FOREIGN PATENT DOCUMENTS

CN    1496714 A    5/2004
CN    1533739 A    10/2004
(Continued)

OTHER PUBLICATIONS

Concurrent Validity, May 21, 2010, Wikipedia, the free encyclopedia, https://en.wikipedia.org/w/index.php?title=Concurrent_validity&oldid=363378403.*

(Continued)

*Primary Examiner* — Stephen R Koziol
*Assistant Examiner* — Raphael Schwartz
(74) *Attorney, Agent, or Firm* — Oblon, McClelland, Maier & Neustadt, L.L.P.

(57) ABSTRACT

A diagnostic reading request system includes: a request information creation unit which creates diagnostic reading request information by adding identification information to clinical image data collected by a medical image diagnostic device; a request information update unit which updates the diagnostic reading request information by adding determination image data having already acquired a diagnostic reading result thereof; a diagnostic reading result evaluation unit which performs, based on a new diagnostic reading result of the determination image data supplied from a diagnostic reading request destination facility, an evaluation of the diagnostic reading result in the diagnostic reading request destination facility; a diagnostic reading report creation unit which creates a diagnostic reading report based on the evaluation of the diagnostic reading result and the diagnostic reading result supplied from the diagnostic reading request destination facility; and a display unit which displays the diagnostic reading report.

14 Claims, 8 Drawing Sheets

(56) References Cited

U.S. PATENT DOCUMENTS

| | | | |
|---|---|---|---|
| 2007/0230763 A1 | | 10/2007 | Matsumoto et al. |
| 2008/0044800 A1 | | 2/2008 | Kanada et al. |
| 2009/0307010 A1* | | 12/2009 | Boehmer-Lasthaus et al. . 705/2 |

FOREIGN PATENT DOCUMENTS

| | | | | |
|---|---|---|---|---|
| CN | 101052352 A | | | 10/2007 |
| CN | 101106939 A | | | 1/2008 |
| JP | 2008-9589 A | | | 1/2008 |
| JP | 2009-45121 A | | | 3/2009 |
| JP | 2009-75951 A | | | 4/2009 |
| JP | 2009075951 A | | * | 4/2009 |

OTHER PUBLICATIONS

Encryption, May 31, 2010, Wikipedia, the free encyclopedia, https://en.wikipedia.org/w/index.php?title=Encryption&oldid=365323577.*

Jin, Hai, et al. "Content and semantic context based image retrieval for medical image grid." Proceedings of the 8th IEEE/ACM International Conference on Grid Computing. IEEE Computer Society, 2007.*

Briggs, Water Quality Monitoring—A Practical Guide to the Design and Implementation of Freshwater Quality Studies and Monitoring Programmes—Chapter 9—Analytical Quality Assurance, United Nations Environment Programme and the World Health Organization,1996.*

Combined Office Action and Search Report issued on Jun. 3, 2015 in Chinese Patent Application No. 201180028066.6 with English translation of category of cited documents.

International Search Report mailed on Jan. 10, 2012, issued for International Application No. PCT/JP2011/073226, filed on Oct. 7, 2011 (English).

Combined International Search Report and Written Opinion issued Jan. 10, 2012 in PCT/JP2011/073226 filed Oct. 7, 2011 (with English translation of category of cited documents).

* cited by examiner

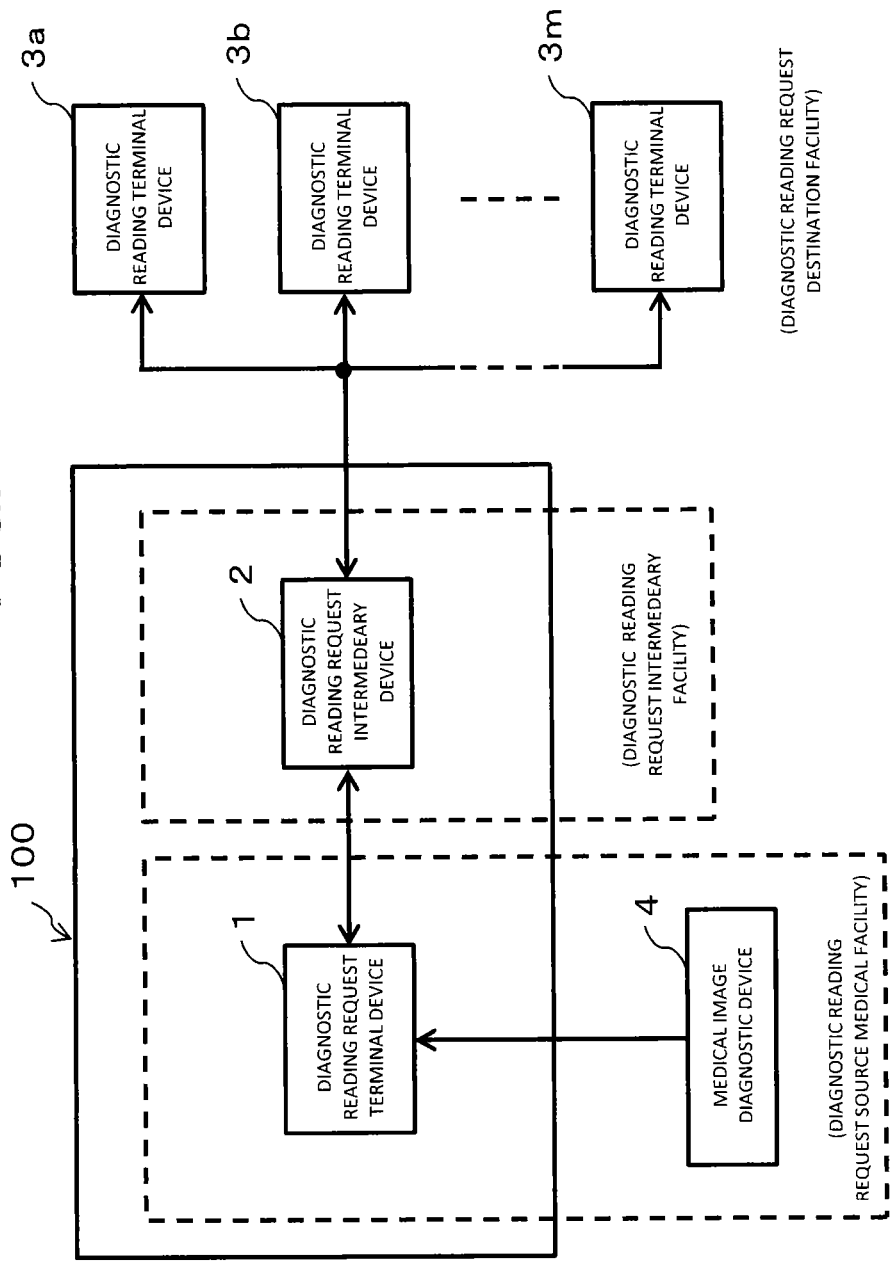

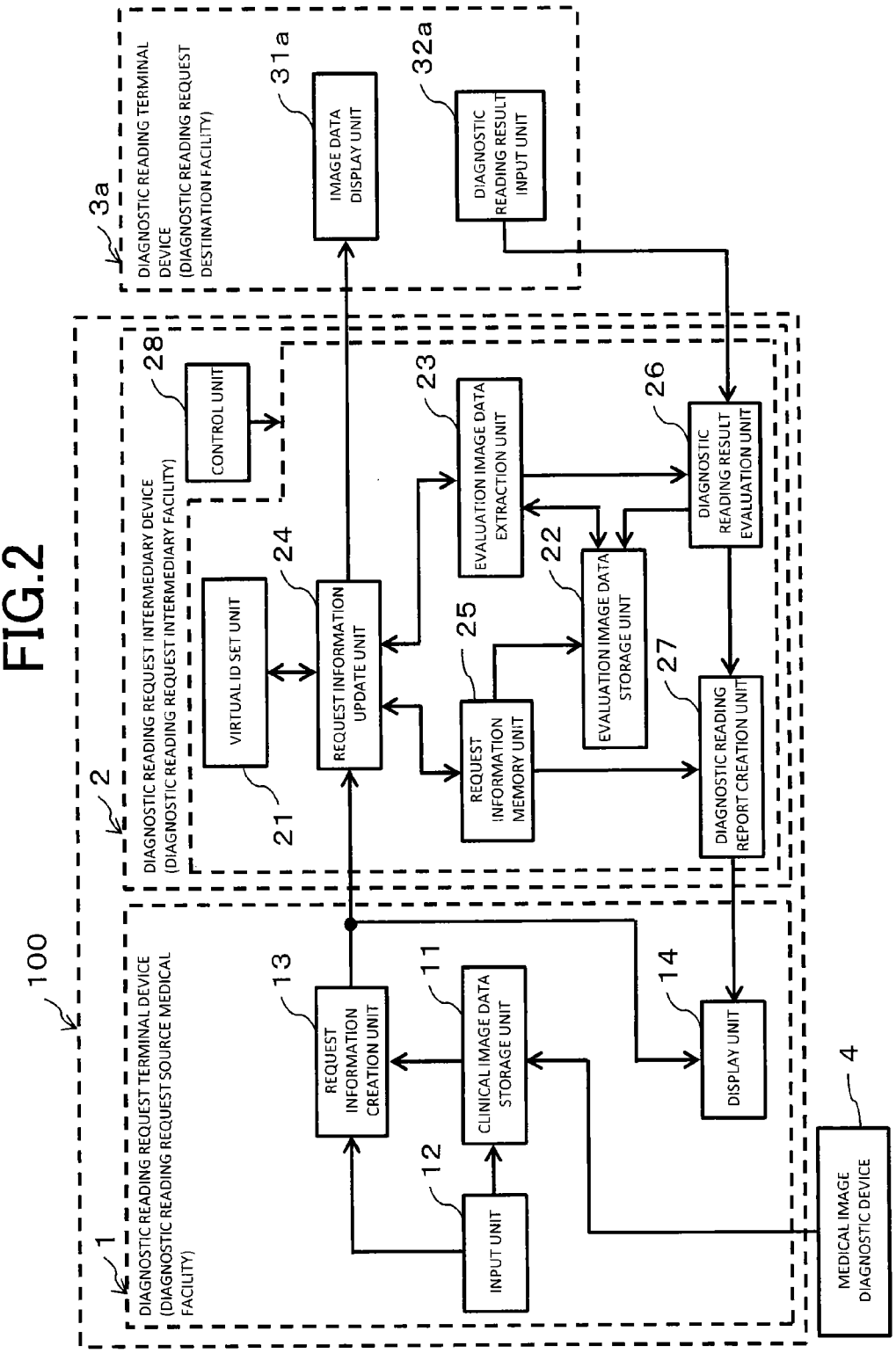

FIG.3

| DIAGNOSTIC READING REQUEST ID |
|---|
| DIAGNOSTIC READING REQUEST DESTINATION FACILITY ID |
| DIAGNOSTIC READING REQUEST SOURCE MEDICAL FACILITY ID |
| SUBJECT INFORMATION<br>    SUBJECT NAME<br>    SUBJECT ID<br>    AGE, GENDER |
| EXAMINATION INFORMATION<br>    ORGAN TO BE EXAMINED<br>    EXAMINATION MODALITY<br>    EXAMINATION DATE |
| IMAGE ID |
| CLINICAL IMAGE DATA |
| DIAGNOSTIC READING RESULT EVALUATION REQUEST |

FIG.4

| DIAGNOSTIC READING REQUEST ID |
|---|
| DIAGNOSTIC READING REQUEST DESTINATION FACILITY ID |
| <u>VIRTUAL DIAGNOSTIC READING REQUEST SOURCE MEDICAL FACILITY ID</u> |
| <u>VIRTUAL SUBJECT ID</u><br>       AGE, GENDER |
| EXAMINATION INFORMATION<br>       ORGAN TO BE EXAMINED<br>       EXAMINATION MODALITY |
| <u>VIRTUAL IMAGE ID</u> |
| CLINICAL IMAGE DATA |
| EVALUATION IMAGE DATA |

FIG.5

| Left table | Right table |
|---|---|
| DIAGNOSTIC READING REQUEST ID | DIAGNOSTIC READING REQUEST ID |
| DIAGNOSTIC READING REQUEST DESTINATION FACILITY ID | DIAGNOSTIC READING REQUEST DESTINATION FACILITY ID |
| DIAGNOSTIC READING REQUEST SOURCE MEDICAL FACILITY ID | VIRTUAL DIAGNOSTIC READING REQUEST SOURCE MEDICAL FACILITY ID |
| SUBJECT INFORMATION<br>  SUBJECT NAME<br>  SUBJECT ID<br>  AGE, GENDER | VIRTUAL SUBJECT INFORMATION<br>  VIRTUAL SUBJECT ID<br>  AGE, GENDER |
| EXAMINATION INFORMATION<br>  ORGAN TO BE EXAMINED<br>  EXAMINATION MODALITY<br>  EXAMINATION DATE | EXAMINATION INFORMATION<br>  ORGAN TO BE EXAMINED<br>  EXAMINATION MODALITY |
| IMAGE ID | VIRTUAL IMAGE ID |
| CLINICAL IMAGE DATA | CLINICAL IMAGE DATA |
| DIAGNOSTIC READING RESULT EVALUATION REQUEST | EVALUATION IMAGE DATA |

FIG.6

| REFERENCE DIAGNOSTIC READING RESULT | X | 800pixel |
|---|---|---|
| | Y | 500pixel |
| | R | 100pixel |
| NEW DIAGNOSTIC READING RESULT | x | 300pixel |
| | y | 200pixel |
| | r | 20pixel |
| DATA SIZE OF IMAGE | S | 1024pixel |
| WEIGHTING COEFFICIENT | W1 | 70% |
| | W2 | 30% |
| ⋮ | ⋮ | ⋮ |
| MATCHING DEGREE | Score | 57.8 |

FIG.8

| DIAGNOSTIC READING REQUEST DESTINATION FACILITY ID | EXAMINATION MODADLITY | ORGAN TO BE EXAMINED | EVALUATION OF DIAGNOSTIC READING RESULT (MATCHING DEGREE SCORE) | TOOL | ACCEPTABLE FOR REQUEST AT NIGHT | ACCEPTABLE FOR REQUEST IN EMERGENCY | COST | REMARKS |
|---|---|---|---|---|---|---|---|---|
| 1001 | CT DEVICE | HEAD | 90 | A | ○ | × | | |
| 1001 | MRI DEVICE | HEAD | 60 | A | ○ | × | | |
| 1002 | MRI DEVICE | CHEST | 55 | C | × | ○ | | |
| 1002 | MRI DEVICE | WHOLE BODY | 90 | C | × | ○ | | |
| 1003 | X-RAY DEVICE | CHEST | 70 | B | ○ | ○ | | |
| ... | ... | ... | ... | ... | ... | ... | ... | ... |

DIAGNOSTIC READING REQUEST SYSTEM, DIAGNOSTIC READING REQUEST INTERMEDIARY DEVICE, CONTROL PROGRAM, AND DIAGNOSTIC READING RESULT EVALUATION METHOD

CROSS-REFERENCE TO THE RELATED APPLICATION

This application is based on and claims the benefit of priority from Japanese Patent Application No. 2010-227988, filed on Jul. 10, 2010; the entire contents of which are incorporated herein by reference.

FIELD

Embodiments of the present invention relate to a diagnostic reading request system, a diagnostic reading request intermediary device, a control program, and a diagnostic reading result evaluation method which allow a person in charge of diagnostic reading in a diagnostic reading request destination facility to evaluate a diagnostic reading result.

BACKGROUND

Medical image diagnoses have been rapidly developed with X-ray CT devices, MRI devices, and the like which are practically utilized along the development of computer technologies, and have become essential for current medical care. In particular, in recent X-ray CT devices or MRI devices, an increase in speed and performance of a biological information detection unit and a calculation process unit makes it possible to collect volume data and generate three-dimensional image data and MPR (Multi Planar Reconstruction) image data using the volume data in a shorter time. Such practical utilization of medical image diagnostic devices enables early detection of a malignant tumor or the like, and thus greatly contributes to decision of a treatment strategy or a treatment method.

Such medical image diagnostic devices having high performance are being widely spread especially in medically advanced countries including Japan. However, because of a shortage of physicians in recent years and the like, a serious problem has occurred that a sufficient number of medical specialists cannot be secured who are capable of diagnostically reading various kinds of image data collected by these medical image diagnostic devices.

Accordingly, a so-called remote medical image diagnostic reading method is starting to be practiced. This is a method in which image data collected by the abovementioned medical image diagnostic devices is transmitted to external diagnostic reading facilities connected via a network or the like, and diagnostic reading of the image data is requested to persons in charge of diagnostic reading who belong to these diagnostic reading facilities. Moreover, in order to reduce a cost required for the diagnostic reading, discussed is a method in which the abovementioned diagnostic reading is requested to overseas diagnostic reading facilities where labor costs for medical staff are lower.

In such remote medical image diagnostic reading method in which diagnostic reading of image data collected by medical image diagnostic devices is requested to external diagnostic reading facilities including overseas diagnostic reading facilities, it becomes important to maintain the quality of diagnostic reading by constantly grasping the diagnostic reading level (diagnostic reading ability) of persons in charge of diagnostic reading who are in charge of diagnostic reading of the image data in the diagnostic reading facilities.

However, it is difficult in reality to correctly grasp the diagnostic reading level of persons in charge of diagnostic reading at remote locations. In particular, it is more difficult to grasp the diagnostic reading level of a requested person in charge of diagnostic reading, because, in overseas diagnostic reading facilities, persons in charge of diagnostic reading change carries more frequently among the facilities. Accordingly, there has been a problem in that the accuracy of a medical diagnosis performed based on the diagnostic reading result provided from the diagnostic reading facilities is dropped.

BRIEF DESCRIPTION OF THE DRAWINGS

FIG. 1 is a diagram illustrating a schematic configuration of a diagnostic reading request system and diagnostic reading terminal devices connected to the diagnostic reading request system according to one embodiment;

FIG. 2 is a block diagram illustrating a concrete configuration of the diagnostic reading request system and the diagnostic reading terminal device according to the embodiment;

FIG. 3 is a view illustrating a concrete example of diagnostic reading request information created by a request information creation unit according to the embodiment;

FIG. 4 is a view illustrating a concrete example of the diagnostic reading request information updated by a request information update unit according to the embodiment;

FIG. 5 is a view for explaining the diagnostic reading request information before update and the diagnostic reading request information after update which are stored in an information memory unit according to the embodiment;

FIG. 6 is a view illustrating concrete values of various kinds of parameters used for calculation of a matching degree score according to the embodiment;

FIG. 8 is a view illustrating a concrete example of diagnostic reading result evaluation list data created by a diagnostic reading report creation unit according to a modification example of the embodiment.

DETAILED DESCRIPTION

Figure 7:
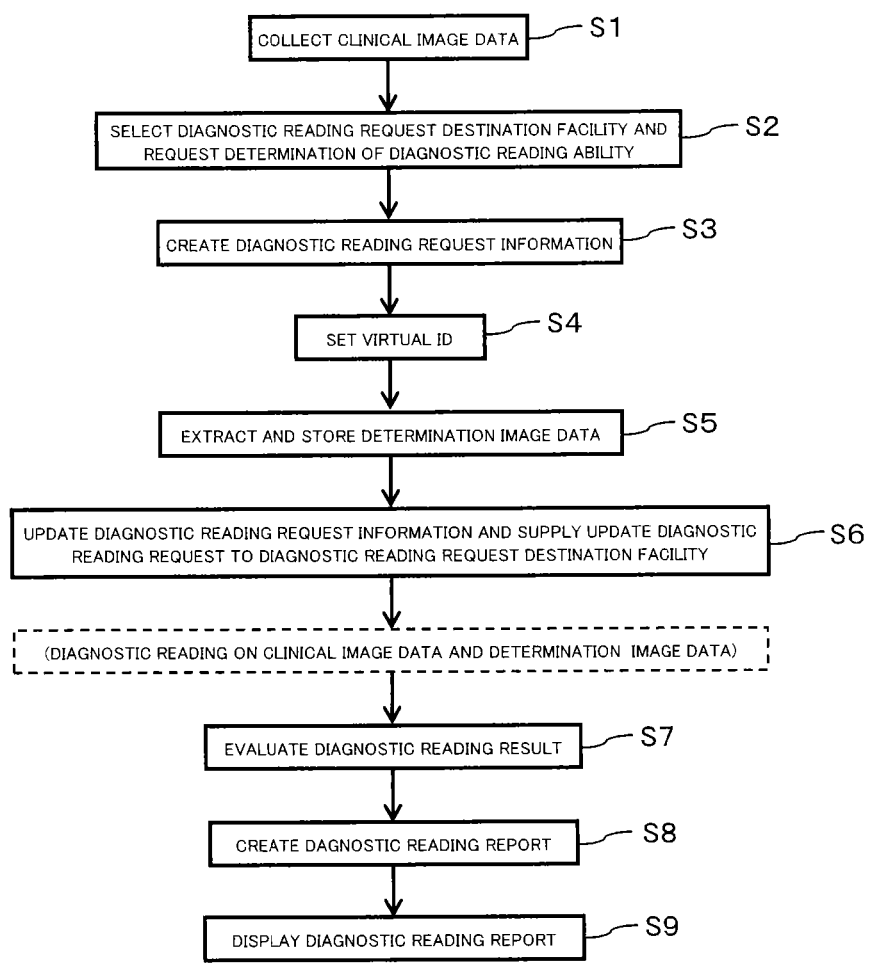
FIG. 7 is a flowchart illustrating an evaluation procedure of a diagnostic reading result according to the embodiment.

According to one embodiment, a diagnostic reading request system which requests diagnostic reading of clinical image data collected by a medical image diagnostic device to a diagnostic reading request destination facility connected thereto via a network, includes: a request information creation unit which creates diagnostic reading request information by adding various kinds of identification information to the clinical image data; a request information update unit which updates the diagnostic reading request information by adding determination image data associated with a reference diagnostic reading result; a diagnostic reading result evaluation unit which performs an evaluation of a diagnostic reading result in the diagnostic reading request destination facility which is included in the diagnostic reading request information after update, based on the diagnostic reading result of the determination image data in the diagnostic reading request destination facility and the reference diagnostic reading result; and an output unit which outputs at least the evaluation of the diagnostic reading result.

Various Embodiments will be described hereinafter with reference to the accompanying drawings.

(Configuration of System)

The configuration and the function of a diagnostic reading request system according to one embodiment of the present disclosure will be described using FIG. 1 to FIG. 6. FIG. 1 is a diagram illustrating a schematic configuration of a diagnostic reading request system and diagnostic reading terminal devices connected to the diagnostic reading request system according to the embodiment. FIG. 2 is a block diagram illustrating a concrete configuration of the diagnostic reading request system and the diagnostic reading terminal device.

A diagnostic reading request system 100 shown in FIG. 1 includes a diagnostic reading request terminal device 1 placed in a diagnostic reading request source medical facility, and a diagnostic reading request intermediary device 2 placed in a diagnostic reading request intermediary facility. The diagnostic reading request terminal device 1 has a function of requesting diagnostic reading (that is, determination of the presence or absence or the extent of an abnormal part by observation of the medical image data) of medical image data collected by a medical image diagnostic device 4 such as an X-ray CT device or an MRI device, to diagnostic reading terminal devices 3a to 3m in a diagnostic reading request destination facility connected thereto via a network or the like.

The diagnostic reading request intermediary device 2 included in the diagnostic reading request system 100 is supplied with the abovementioned medical image data and diagnostic reading request information from the diagnostic reading request terminal device 1. The diagnostic reading request intermediary device 2 supplies, to a diagnostic reading terminal device 3 in the diagnostic reading request destination facility corresponding to a diagnostic reading request destination facility ID indicated by the diagnostic reading request information, the medical image data (hereinafter, referred to as "clinical image data"), and medical image data (hereinafter, referred to as, "determination image data") which corresponds to the clinical image data and has already acquired a correct diagnostic reading result.

Next, the diagnostic reading request intermediary device 2 receives diagnostic reading results to the clinical image data and the determination image data which are supplied from the diagnostic reading terminal device 3. The diagnostic reading request intermediary device 2 compares the diagnostic reading result (hereinafter, referred to as "new diagnostic reading result") to the determination image data, which is newly acquired from the diagnostic reading request destination facility, with the diagnostic reading result (hereinafter, referred to as "reference diagnostic reading result") in which the adequacy of the diagnostic reading to the determination image data has been already confirmed in the previous, to evaluate the diagnostic reading result in the diagnostic reading request destination facility. The diagnostic reading request intermediary device 2 then supplies the determination result and the diagnostic reading result of the clinical image data to the diagnostic reading request terminal device 1 in the diagnostic reading request source medical facility.

Further, in the embodiment, the diagnostic reading request terminal device 1 and the diagnostic reading request intermediary device 2 which constitute the diagnostic reading request system 100 are placed, as shown in FIG. 1, in the diagnostic reading request source medical facility and the diagnostic reading request intermediary facility which are remotely connected thereto via a network, respectively.

Further, the medical image diagnostic device 4 is placed in the diagnostic reading request source medical facility together with the diagnostic reading request terminal device 1.

Note that, the configuration of the diagnostic reading request system 100 is not limited thereto, for example, the diagnostic reading request terminal device 1 and the diagnostic reading request intermediary device 2 may be placed in the same diagnostic reading request source medical facility. In addition, for example, the medical image diagnostic device 4 can be placed in another medical facility different from the diagnostic reading request source medical facility.

Next, a concrete configuration and functions of the diagnostic reading request system 100 will be described using the block diagram of FIG. 2. Further, in FIG. 2, described is a case where a diagnostic reading request destination facility having the diagnostic reading terminal device 3a is selected from among multiple diagnostic reading request destination facilities in which the diagnostic reading terminal devices 3a to 3m are placed, and diagnostic reading of clinical image data is request to the diagnostic reading request destination facility. Note that, diagnostic reading may be requested to another diagnostic reading request destination facility.

As already shown in FIG. 1, the diagnostic reading request system 100 has the diagnostic reading request terminal device 1 that is a diagnostic reading request source medical facility, and the diagnostic reading request intermediary device 2 that is a diagnostic reading request intermediary facility. The diagnostic reading request intermediary device 2 is connected, via a network or the like, to the diagnostic reading request terminal device 1, and the diagnostic reading terminal device 3a in the diagnostic reading request destination facility.

The diagnostic reading request terminal device 1 in the diagnostic reading request system 100 includes a clinical image data storage unit 11, an input unit 12, a request information creation unit 13, and a display unit 14.

The clinical image data storage unit 11 has an unillustrated data memory unit. The data memory unit stores therein clinical image data of a target subject and supplementary information thereof which are supplied from the medical image diagnostic device 4 placed separately via a network, a large-capacity memory medium, or the like (hereinafter, collectively referred to as "network"). Further, the supplementary information of the clinical image data includes: subject information such as a subject name, a subject ID, and an age and a gender; examination information such as an examination date, an organ to be examined, and an examination modality; an image ID; and the like.

The input unit 12 includes an input device, such as a display panel, a switch, a key board, or a mouse, on an operation console. A diagnostic reading request ID, a subject ID, a diagnostic reading request source medical facility ID, a diagnostic reading request destination facility ID, and an image ID are inputted and various kinds of instruction signals are inputted, through the input unit 12. Moreover, the supplementary information mentioned above is reregistered or a diagnostic reading result evaluation request is inputted therethrough, if necessary. In response to an input of the diagnostic reading request destination facility ID, a desired diagnostic reading request destination facility (for example, here, a diagnostic reading request destination facility having the diagnostic reading terminal device 3a) corresponding to the diagnostic reading request destination facility ID is selected from among multiple diagnostic reading request destination facilities.

The request information creation unit 13 creates diagnostic reading request information as shown in FIG. 3, for example. The diagnostic reading request information includes the diagnostic reading request ID, the diagnostic reading request destination facility ID, the diagnostic reading request source medical facility ID, the image ID, and the diagnostic reading result evaluation request, which are inputted in the input unit 12. The diagnostic reading request information further includes the clinical image data of the subject, and the subject information (the subject name, the subject ID, and the age and the gender) and the examination information (the organ to be examined, an examination modality and the examination date) added to the image data, which are read out from the clinical image data storage unit 11.

Referring back to FIG. 2, the display unit 14 in the diagnostic reading request terminal device 1 has a function of displaying diagnostic reading request information created by the request information creation unit 13, a diagnostic reading report supplied from the diagnostic reading request intermediary device 2, or the like. Further, the display unit 14 includes a display data generation unit, a data conversion unit, and a monitor, which are not illustrated.

The display data generation unit converts diagnostic reading request information supplied from the request information creation unit 13 or a diagnostic reading report supplied from the diagnostic reading request intermediary device 2 into a predetermined display format to generate display data. The data conversion unit performs conversion processing, such as D/A conversion or television format conversion, on the display data generated by the display data generation unit to display the display data thus converted on the monitor.

Next, the diagnostic reading request intermediary device 2 in the diagnostic reading request intermediary facility includes a virtual ID set unit 21, a determination image data storage unit 22, a determination image data extraction unit 23, a request information update unit 24, and a request information memory unit 25. The diagnostic reading request intermediary device 2 further includes a diagnostic reading result evaluation unit 26, a diagnostic reading report creation unit 27, and a control unit 28.

The virtual ID set unit 21 receives a diagnostic reading request source medical facility ID, a subject ID, and an image ID which are included in the diagnostic reading request information before update supplied from the request information creation unit 13 in the diagnostic reading request terminal device 1 through the request information update unit 24. The virtual ID set unit 21 then sets virtual IDs (virtual identification information), such as a virtual diagnostic reading request source medical facility ID, a virtual subject ID, a virtual image ID, to these IDs (identification information).

Note that, among information included in the subject ID, virtual subject IDs are not set to "an age and a gender".

Meanwhile, the determination image data storage unit 22 stores therein in advance determination image data of the target subject or another subjects which are collected using various kinds of medical image diagnostic devices (examination modalities) and has already acquired a correct diagnostic reading result. The determination image data includes data including image data itself, the presence or absence of a disease (case) indicated by the image data, a position of the case in the image data, or a part (organ to be examined) where the case is present. A diagnostic reading result (the abovementioned reference diagnostic reading result) and various kinds of examination information (for example, an organ to be examined and an examination modality) are further added to the determination image data as supplementary information.

The determination image data extraction unit 23 includes an image data memory unit and a diagnostic reading result memory unit, which are not illustrated. The determination image data extraction unit 23 extracts determination image data corresponding to the clinical image data of the diagnostic reading request information supplied from the request information creation unit 13 in the diagnostic reading request terminal device 1, from among the various kinds of determination image data stored in the determination image data storage unit 22. Specifically, the determination image data extraction unit 23 firstly receives, as supplementary information of clinical image data mentioned above, examination information (an organ to be examined and an examination modality) of the diagnostic reading request information supplied from the request information creation unit 13 through the request information update unit 24. The determination image data extraction unit 23 then extracts determination image data having examination information the same or similar to the received examination information, from among the abovementioned various kinds of the determination image data. The determination image data extraction unit 23 then stores the acquired determination image data in the image data memory unit, and stores a reference diagnostic reading result added to the determination image data in the diagnostic reading result memory unit.

Next, the request information update unit 24 changes the diagnostic reading request source medical facility ID, the subject ID, and the image ID which are added to the clinical image data of the diagnostic reading request information supplied from the request information creation unit 13 in the diagnostic reading request terminal device 1 to the virtual diagnostic reading request source medical facility ID, the virtual subject ID, and the virtual image ID which are supplied from the virtual ID set unit 21, respectively. Note that, as mentioned above, each piece of information about "an age and a gender" is not changed (set) to a virtual subject ID. This is because these pieces of information are information to be required at diagnostic reading, Further, it is considered that these pieces of information alone may not be information with which a person can be identified.

Further, the request information update unit 24 updates the diagnostic reading request information (refer to FIG. 3) created by the request information creation unit 13, by adding the determination image data read out from the image data memory unit in the determination image data extraction unit 23 thereto. Specifically, in the diagnostic reading request information after update, the diagnostic reading request ID and the diagnostic reading request destination facility ID which are included in the diagnostic reading request information before update remain without any change, while the diagnostic reading request source medical facility ID, the subject ID, and the image ID with which a diagnostic reading request source medical facility, a subject, and clinical image data can be identified are eliminated.

FIG. 4 is a view illustrating a concrete example of diagnostic reading request information updated by the request information update unit 24. The diagnostic reading request information after update includes the diagnostic reading request ID and the diagnostic reading request destination facility ID which are inputted in the input unit 12, the virtual diagnostic reading request source medical facility ID, the virtual subject ID, and the virtual image ID which are set by the virtual ID set unit 21, the clinical image data, and the determination image data. In addition, as shown in FIG. 4, examination information, such as an organ to be examined or an examination modality, with which diagnostic reading in the diagnostic reading request destination facility is supported may be added thereto.

The request information update unit 24 supplies the updated diagnostic reading request information to the diagnostic reading terminal device 3a in the diagnostic reading request destination facility connected thereto via the network or the like.

Referring back to FIG. 2 again, the request information memory unit 25 in the diagnostic reading request intermediary device 2 stores therein the diagnostic reading request information before update supplied from the request information creation unit 13 through the request information update unit 24 and the diagnostic reading request information updated by the request information update unit 24 in such a manner as to be associated with each other.

FIG. 5 indicates the diagnostic reading request information before update stored in the request information memory unit 25 in the left side thereof, and the diagnostic reading request information after update in the right side thereof. For example, as is the case of FIG. 5, the diagnostic reading request information before update shown in FIG. 3 and the diagnostic reading request information after update shown in FIG. 4 may be stored without any change. Alternatively, only the updated diagnostic reading request information (that is, the virtual diagnostic reading request source medical facility ID, the virtual subject ID, and the virtual image ID) and the added determination image data are added to the diagnostic reading request information before update.

Next, the diagnostic reading result evaluation unit 26 in the diagnostic reading request intermediary device 2, shown in FIG. 2, receives the following information from the diagnostic reading terminal device 3a in the diagnostic reading request destination facility. Specifically, the diagnostic reading result evaluation unit 26 receives diagnostic reading results with respect to the clinical image data and the determination image data performed by a person in charge of diagnostic reading in the diagnostic reading request destination facility based on the abovementioned updated diagnostic reading request information, as well as the diagnostic reading request ID, the diagnostic reading request destination facility ID, the virtual diagnostic reading request source medical facility ID, the virtual subject ID, and the virtual image ID, which are supplementary information thereof. The diagnostic reading result evaluation unit 26 then compares the reference diagnostic reading result of the determination image data stored in the diagnostic reading result memory unit in the determination image data extraction unit 23 with the new diagnostic reading result of the determination image data newly supplied from the diagnostic reading terminal device 3a, to evaluate the diagnostic reading results by the diagnostic reading request destination facility.

Specifically, the diagnostic reading result evaluation unit 26 uses a matching degree score (Score) of the new diagnostic reading result with respect to the reference diagnostic reading result which is calculated based on the presence or absence, a position, a size (radius), and the like of an abnormal part indicated in observations of the reference diagnostic reading result and the new diagnostic reading result mentioned above, to evaluate the diagnostic reading result by the diagnostic reading request destination facility. For example, in a case where position coordinates and a radius of an abnormal part in the reference diagnostic reading result is (X, Y) and R, and position coordinates and a radius of the abnormal part in the new diagnostic reading result are (x, y) and r, a matching degree score of the new diagnostic reading result with respect to the reference diagnostic reading result can be calculated, for example, by a formula (1) below.

$$\text{Score} = \text{Dif} \times \left( \left( 1 - \frac{\sqrt{(X-x)^2 + (Y-y)^2}}{S} \right) \times W1 + \left( 1 - \frac{|R-r|}{S} \right) \times W2 \right) \times 100 \quad (1)$$

Note that, in the formula (1), W1 weighting is applied on the matching degree of the position coordinates, and W2 weighting is applied on the matching degree of the sizes (radiuses). Further, "S" and "Dif" which are indicated in the formula (1) represent a parameter about image sizes of the clinical image data and the determination image data and a count depending on the presence or absence of the abnormal part, respectively.

For example, if the presence or absence of an abnormal part in the observation of the reference diagnostic reading result matches with the presence or absence of the abnormal part in the observation of the new diagnostic reading result, "Dif=1" is set, and if not, "Dif=0" is set.

FIG. 6 indicates position coordinates and radiuses of abnormal parts in the observations of the reference diagnostic reading result and the new diagnostic reading result, weighting coefficients with respect to these position coordinates and radiuses, a concrete value of the image size, and a matching degree score calculated with these values.

The diagnostic reading result evaluation unit 26 determines that an evaluation of the diagnostic reading result in the diagnostic reading request destination facility is "good" if the matching degree score exceeds a predetermined threshold value γ, and determines that the evaluation is "failure" if the matching degree score does not exceed the predetermined threshold value γ. The diagnostic reading result evaluation unit 26 then supplies the determination result and the abovementioned matching degree score together with the diagnostic reading result to the clinical image data to the diagnostic reading report creation unit 27.

On the other hand, if an evaluation of the diagnostic reading result in the diagnostic reading request destination facility is "good", the diagnostic reading result evaluation unit 26 stores the clinical image data included in the diagnostic reading request information before update or after update which is read out from the request information memory unit 25, and the diagnostic reading result with respect to the clinical image data supplied from the diagnostic reading terminal device 3a in the diagnostic reading request destination facility, in the determination image data storage unit 22. In other words, the clinical image data diagnostically read by the diagnostic reading request destination facility with an evaluation of the diagnostic reading result being a predetermined level or higher, and the diagnostic reading result thereof are stored in the determination image data storage unit 22, and are used as determination image data in the next and the following evaluations of diagnostic reading results.

Next, the diagnostic reading report creation unit 27 shown in FIG. 2 creates a diagnostic reading report based on the diagnostic reading result to the clinical image data supplied from the diagnostic reading terminal device 3a through the diagnostic reading result evaluation unit 26, the evaluation of the diagnostic reading result and the matching degree score which are supplied from the diagnostic reading result evaluation unit 26, and the like. At this time, the diagnostic reading report creation unit 27 converts the virtual diagnostic reading request source medical facility ID, the virtual subject ID, and the virtual image ID which are added to the diagnostic reading result to the clinical image data based on the diagnostic reading request information before update and the diagnostic reading request information after update which are read out from the request information memory unit 25, to update to the diagnostic reading request source medical facility ID, the subject ID, and the image ID of the diagnostic reading request information before update, respectively. In other words, the diagnostic reading report creation unit 27 recovers the virtual IDs (virtual identification information) having been set by the virtual ID set unit 21 to the original IDs (identification information), and creates the abovementioned diagnostic reading report using these IDs thus recovered.

The control unit 28 includes, for example, a CPU and a control program storage unit, which are not illustrated. The control program storage unit stores in advance therein a control program for evaluating a diagnostic reading result in the diagnostic reading request destination facility based on the reference diagnostic reading result and the new diagnostic reading result of the determination image data. Meanwhile, the CPU collectively controls the respective units in the diagnostic reading request intermediary device 2 based on the control program read out from the abovementioned control program storage unit, and causes the respective units to execute an evaluation of the diagnostic reading result with respect to the diagnostic reading request destination facility.

Next, the diagnostic reading terminal device 3a in the diagnostic reading request destination facility connected to the diagnostic reading request system 100 according to the embodiment via the network includes an image data display unit 31a and a diagnostic reading result input unit 32a. The diagnostic reading terminal device 3a further has a function of displaying the clinical image data and the determination image data which are supplied from the diagnostic reading request intermediary device 2 in the diagnostic reading request system 100, and inputting diagnostic reading results with respect to these pieces of image data.

In other words, the image data display unit 31a in the diagnostic reading terminal device 3a includes a display data generation unit, a data conversion unit, and a monitor, which are not illustrated. The display data generation unit converts each of the clinical image data and the determination image data which are included in the diagnostic reading request information after update supplied from the request information update unit 24 in the diagnostic reading request intermediary device 2 into a predetermined display format to generate display data. The data conversion unit performs conversion processing, such as D/A conversion or television format conversion on the display data generated by the display data generation unit to display the display data thus converted on the monitor.

Meanwhile, the diagnostic reading result input unit 32a includes input devices, such as a display panel, a switch, a key board, and a mouse, on an operation console. The results of diagnostic reading with respect to the clinical image data and the determination image data which is performed by a person in charge of diagnostic reading in the diagnostic reading request destination facility are inputted using the input device or the display panel mentioned above.

(Evaluation Procedure of Diagnostic Reading Result)

Next, an evaluation procedure of the diagnostic reading result according to the embodiment will be described using a flowchart in FIG. 7. Further, in the procedure indicated below, described is a case where an evaluation of the diagnostic reading result in the diagnostic reading request destination facility is performed in response to a diagnostic reading result evaluation request inputted in the input unit 12 in the diagnostic reading request terminal device 1. Note that an evaluation of the diagnostic reading result in the diagnostic reading request destination facility may be performed alternatively in response to a diagnostic reading result evaluation instruction signal generated in the control unit 28 in the diagnostic reading request intermediary device 2 at a desired timing.

Prior to a diagnostic reading request of clinical image data to a diagnostic reading request destination facility, clinical image data of a subject is collected in advance by the medical image diagnostic device 4, such as an X-ray CT device or an MRI device, which is separately placed. The clinical image data of the subject includes subject information and examination information as supplementary information, and is stored in the clinical image data storage unit 11 included in the diagnostic reading request terminal device 1 in the diagnostic reading request system 100 via a network, a large-capacity memory medium, or the like (Step S1 in FIG. 7).

After the clinical image data and the supplementary information thereof are stored in the clinical image data storage unit 11, a medical staff of the diagnostic reading request terminal device 1 firstly inputs a diagnostic reading request ID, a diagnostic reading request source medical facility ID, and a subject ID in the input unit 12. The medical staff then inputs a diagnostic reading request destination facility ID and an evaluation request of a diagnostic reading result to select a diagnostic reading request destination facility having the diagnostic reading terminal device 3a from among multiple diagnostic reading request destination facilities, and requests an evaluation of a diagnostic reading result to the diagnostic reading request destination facility (Step S2 in FIG. 7).

Meanwhile, the request information creation unit 13 reads out, based on the subject ID inputted in the input unit 12, the clinical image data of the subject and the supplementary information thereof from the clinical image data storage unit 11. The request information creation unit 13 then adds information such as the diagnostic reading request ID, the diagnostic reading request destination facility ID, the diagnostic reading request source medical facility ID, the image ID, and the diagnostic reading result evaluation request, which are similarly inputted in the input unit 12, to the clinical image data of the subject and the supplementary information thereof, to create diagnostic reading request information (Step S3 in FIG. 7).

Next, the virtual ID set unit 21 in the diagnostic reading request intermediary device 2 receives the supplementary information of the diagnostic reading request source medical facility ID, the subject ID, and the image ID included in the diagnostic reading request information before update. The diagnostic reading request information before update is supplied from the request information creation unit 13 in the diagnostic reading request terminal device 1 through the request information update unit 24 to the virtual ID set unit 21. The virtual ID set unit 21 sets virtual IDs (virtual identification information) such as a virtual diagnostic reading request source medical facility ID, a virtual subject ID, and a virtual image ID to these IDs thus supplied (identification information) (Step S4 in FIG. 7).

Meanwhile, the determination image data extraction unit 23 receives, as the supplementary information of the clinical image data, the examination information (for example, an organ to be examined and an examination modality) in the diagnostic reading request information. The examination information in the diagnostic reading request information is supplied from the request information creation unit 13 through the request information update unit 24 to the determination image data extraction unit 23. The determination image data extraction unit 23 extracts determination image data having examination information the same or similar to the examination information thus supplied from among various kinds of determination image data stored in the determination image data storage unit 22. The determination image data extraction unit 23 then stores the acquired determination image data in the image data memory unit thereof, and stores a reference diagnostic reading result added to the determination image data in the diagnostic reading result memory unit thereof (Step S5 in FIG. 7).

Next, the request information update unit 24 receives the clinical image data of the diagnostic reading request information supplied from the request information creation unit 13 in the diagnostic reading request terminal device 1. The request information update unit 24 then changes the diagnostic reading request source medical facility ID, the subject ID, and the image ID which are added to the clinical image data of the diagnostic reading request information to the virtual diagnostic reading request source medical facility ID, the virtual subject ID, and the virtual image ID which are supplied from the virtual ID set unit 21, respectively. Further, the request information update unit updates the diagnostic reading request information created by the request information creation unit 13, by adding the determination image data read out from the image data memory unit in the determination image data extraction unit 23 to the clinical image data of the diagnostic reading request information. The request information update unit 24 then supplies the updated diagnostic reading request information to the diagnostic reading terminal device 3a in the diagnostic reading request destination facility connected thereto via the network or the like (Step S6 in FIG. 7).

Note that, the request information update unit 24 supplies the diagnostic reading request information to the diagnostic reading terminal device 3a in the diagnostic reading request destination facility automatically with a predetermined time interval as appropriate.

Further, the diagnostic reading request information before update supplied from the request information creation unit 13 and the diagnostic reading request information updated by the request information update unit 24 are stored in the request information memory unit 25.

Next, a person in charge of diagnostic reading in the diagnostic reading request destination facility who has received the diagnostic reading request information after update displays the clinical image data and the determination image data which are included the diagnostic reading request information on the image data display unit 31a in the diagnostic reading terminal device 3a, to perform diagnostic reading on the clinical image data and the determination image data (which is indicated in FIG. 7 as an area surrounded by the dashed line). The person in charge of diagnostic reading then input diagnostic reading results thereof in the diagnostic reading result input unit 32a. At this time, the diagnostic reading request ID, the diagnostic reading request destination facility ID, the virtual diagnostic reading request source medical facility ID, the virtual subject ID, the virtual image ID, and the like, which are added to the clinical image data and the determination image data mentioned above, are inputted together with the diagnostic reading result to the clinical image data and the diagnostic reading result to the determination image data (new diagnostic reading result).

Meanwhile, the diagnostic reading result evaluation unit 26 in the diagnostic reading request intermediary device 2 receives the abovementioned diagnostic reading results with respect to the clinical image data and the determination image data, and the supplementary information thereof. The diagnostic reading result evaluation unit 26 compares the reference diagnostic reading result of the determination image data read out from the diagnostic reading result memory unit in the determination image data extraction unit 23 with the new diagnostic reading result supplied from the diagnostic reading request destination facility, to evaluate the diagnostic reading result in the diagnostic reading request destination facility (Step S7 in FIG. 7).

Note that, the new diagnostic reading result may be added with, for example, information of a diagnostic reading person ID indicating a person in charge of each diagnostic reading, information indicating a date/time or a day of the week when the diagnostically read is performed, or the like. When the diagnostic reading result is evaluated, these pieces of information can be referred. For example, the number of pieces of diagnostic reading by a single diagnostic reading person per day can be grasped from the diagnostic reading person ID. Further, considering information about days of the week when the diagnostic reading results are evaluated enables evaluation per each day of the week.

If an evaluation of the diagnostic reading result in the diagnostic reading request destination facility is determined as "good", the clinical image data included in the diagnostic reading request information before update or the diagnostic reading request information after update read out from the request information memory unit 25, and the diagnostic reading result with respect to the clinical image data supplied from the diagnostic reading request destination facility are stored in the determination image data storage unit 22.

Meanwhile, the diagnostic reading report creation unit 27 creates a diagnostic reading report based on the diagnostic reading result to the clinical image data supplied from the diagnostic reading terminal device 3a through the diagnostic reading result evaluation unit 26, the evaluation result of the diagnostic reading result supplied from the diagnostic reading result evaluation unit 26, and the like. At this time, the diagnostic reading report creation unit 27 updates, based on the diagnostic reading request information before update and the diagnostic reading request information after update read out from the request information memory unit 25, the virtual diagnostic reading request source medical facility ID, the virtual subject ID, and the virtual image ID, which are added to the diagnostic reading result to the clinical image data, to the diagnostic reading request source medical facility ID, the subject ID, and the image ID of the diagnostic reading request information before update, respectively.

In other words, the diagnostic reading report creation unit 27 recovers the virtual IDs (virtual identification information) having been set by the virtual ID set unit 21 to the original IDs (identification information), and creates the abovementioned diagnostic reading report using these original IDs (Step S8 in FIG. 7). Then, the diagnostic reading report created by the diagnostic reading report creation unit 27 is displayed on the display unit 14 in the diagnostic reading request terminal device 1 (Step S9 in FIG. 7).

According to the embodiment of the present disclosure mentioned above, when diagnostic reading of medical image data collected by a medical image diagnostic device is requested to a diagnostic reading request destination facility connected thereto via a network or the like, based on a diagnostic reading result of the medical image data supplied from the diagnostic reading request destination facility, an evaluation of the diagnostic reading result in the diagnostic reading request destination facility can be performed.

In particular, when diagnostic reading of clinical image data newly collected by a medical image diagnostic device is requested to the abovementioned diagnostic reading request destination facility, the clinical image data and determination image data having already acquired a correct diagnostic reading result (reference diagnostic reading result) together are supplied to the diagnostic reading request destination facility. Further, comparing a diagnostic reading result (new diagnostic reading result) to the determination image data with the reference diagnostic reading result makes it possible to easily and correctly determine an evaluation of the diagnostic reading result in the diagnostic reading request destination facility.

Moreover, according to the abovementioned embodiment, instead of IDs with which identification of a diagnostic reading request source medical facility, a subject, clinical image data, and the like is possible, clinical image data added with virtual IDs (identification information) with which identification thereof is impossible and determination image data are supplied to the diagnostic reading request destination facility. Accordingly, a leakage of personal information about a subject or the like in the diagnostic reading request destination facility or identification of the diagnostic reading request source medical facility as a medical facility can be prevented.

In addition, determination image data having supplementary information corresponding to the subject information or the examination information which is added to the clinical image data is extracted from among various kinds of determination image data having been stored in advance separately from the clinical image data. Therefore, a person in charge of diagnostic reading in the diagnostic reading request destination facility can perform diagnostic reading of the clinical image data and the determination image data under the same conditions without knowing the presence of the determination image data which is added in order to evaluate a diagnostic reading result.

Further, according to the abovementioned embodiment, an evaluation of a diagnostic reading result is performed automatically with a predetermined time interval. Alternatively, when the diagnostic reading request source medical facility sets a response deadline about the diagnostic reading result to the clinical image data, the diagnostic reading request intermediary facility requests to the diagnostic reading request destination facility so as to satisfy the response deadline. Accordingly, an evaluation of a diagnostic reading result may be performed with an interval during which the request is performed. Further, determination with a frequency asked by the diagnostic reading request source medical facility is possible. In this manner, because a frequency of an evaluation of a diagnostic reading result can be set as appropriate, a medical staff in the diagnostic reading request source medical facility can easily grasp the current evaluation of the diagnostic reading result in the diagnostic reading request destination facility if necessary, thereby making it possible to always obtain a diagnostic reading result with high accuracy.

In the foregoing, the embodiment of the present disclosure has been described; however, the present disclosure is not limited to the abovementioned embodiment and is possible to carry out by modification. For example, in the abovementioned embodiment, described is a case where the diagnostic reading request terminal device 1 and the diagnostic reading request intermediary device 2 are placed in a diagnostic reading request source medical facility and a diagnostic reading request intermediary facility, respectively, which are remotely connected thereto via a network, and the medical image diagnostic device 4 is placed together with the diagnostic reading request terminal device 1 in the diagnostic reading request source medical facility.

Note that, the diagnostic reading request terminal device 1 and the diagnostic reading request intermediary device 2 may be placed in the same diagnostic reading request source medical facility. Moreover, the medical image diagnostic device 4 can be placed in another medical facility different from the diagnostic reading request source medical facility.

The case has been described where the diagnostic reading report creation unit 27 in the diagnostic reading request intermediary device 2 creates a diagnostic reading report based on the diagnostic reading result to the clinical image data supplied from the diagnostic reading terminal device 3a and the evaluation result of the diagnostic reading result supplied from the diagnostic reading result evaluation unit 26. Note that, the diagnostic reading report may be further added with diagnostic reading result evaluation ranking data, diagnostic reading result evaluation list data as shown in FIG. 8, or the like which indicates, in examination modality unit or in examined organ unit, evaluations of the diagnostic reading results with respect to the clinical image data in the respective diagnostic reading request destination facilities which have been determined in the previous diagnostic reading requests.

FIG. 8 illustrates diagnostic reading result evaluation list data. The list table provides a summary of evaluations of the diagnostic reading results performed for each diagnostic reading request destination facility. A concrete evaluation of the diagnostic reading result is indicated in an "examination modality", an "organ to be examined", and an "evaluation of the diagnostic reading result (matching degree score)". For example, with respect to a diagnostic reading request destination facility indicated by an ID of "1003", an evaluation of a diagnostic reading result when an "X-ray device" is used to examine a "chest" is evaluated as "70". Further, in addition to the concrete evaluation of the diagnostic reading result, the list table shown in FIG. 8 is provided with evaluation items to the diagnostic reading request destination facility including, for example, a "tool (used in diagnostic reading)", "acceptable for request at night", "acceptable for request in emergency", "cost", and "remarks". Note that, the items merely exemplified in the diagnostic reading result evaluation list data, and evaluation items can be arbitrarily set.

In this case, the diagnostic reading report creation unit 27 has, for example, an unillustrated data memory unit and stores therein an evaluation (matching degree score) of a diagnostic reading result to determination image data determined by the diagnostic reading result evaluation unit 26, and a diagnostic reading request destination facility ID, an examination modality ID, and an organ to be examined ID which are added to the determination image data, per unit of a diagnostic reading request destination facility. Further, the diagnostic reading report creation unit 27 reads out these pieces of data from the data memory unit at a predetermined timing to create the diagnostic reading result evaluation ranking data or the diagnostic reading result evaluation list data mentioned above.

Because data such as the diagnostic reading result evaluation ranking data and the diagnostic reading result evaluation list data is provided, the medical staff in the diagnostic reading request source medical facility can easily select an appropriate diagnostic reading request destination facility for diagnostic reading of clinical image data in the next and the following times based on the determination evaluation. Further, based on the data, characteristics or a tendency for each diagnostic reading request destination facility can be grasped. The characteristics or the tendency include, for example, one diagnostic reading request destination facility is good at diagnostic reading about an organ to be examined, or, one diagnostic reading request destination facility can perform diagnostic reading of any organ to be examined at high level. Accordingly, based on the characteristics or the tendency, it is possible in the diagnostic reading request intermediary facility, for example, to automatically assign a diagnostic reading request from the diagnostic reading request source medical facility to an appropriate diagnostic reading request destination facility.

Meanwhile, in the abovementioned embodiment, described is the diagnostic reading request intermediary device 2 which evaluates the diagnostic reading result in the diagnostic reading request destination facility based on the diagnostic reading result evaluation request supplied from the diagnostic reading request terminal device 1. Note that, for example, the diagnostic reading request intermediary device 2 may perform an evaluation of the diagnostic reading result in the diagnostic reading request destination facility based on a diagnostic reading result evaluation instruction signal generated at a desired timing by the control unit 28 in the diagnostic reading request intermediary device 2 or the like. In this case, only when the evaluation of the diagnostic reading result in the diagnostic reading request destination facility does not reach a predetermined level, the diagnostic reading report creation unit 27 may describe a word of warning indicating the fact on a diagnostic reading report, or may create a diagnostic reading report on which all the diagnostic reading results are indicated. Moreover, when no diagnostic reading result evaluation request is supplied or no diagnostic reading result evaluation instruction signal is generated, the diagnostic reading report creation unit 27 may create a diagnostic reading report based on the diagnostic reading result to the clinical image data supplied from the diagnostic reading request destination facility.

In addition, in the abovementioned embodiment, described is a case where an evaluation of the diagnostic reading result in the diagnostic reading request destination facility is automatically performed based on the reference diagnostic reading result and the new diagnostic reading result to the determination image data. Note that, the present invention is not limited thereto, for example, a person in charge in the diagnostic reading request intermediary facility or a medical staff in the diagnostic reading request source medical facility can perform an evaluation of the diagnostic reading result in the diagnostic reading request destination facility based on the reference diagnostic reading result and the new diagnostic reading result mentioned above. In this case, an unillustrated reception unit which receives the diagnostic reading result of the clinical image data and the new diagnostic reading result of the determination image data from the diagnostic reading request destination facility is included at least in either one of the diagnostic reading request terminal device 1 and the diagnostic reading request intermediary device 2.

In addition, although a case where diagnostic reading request information after update to be supplied to the diagnostic reading request destination facility includes examination information, such as an examination modality or an organ to be examined, for supporting diagnostic reading, is indicated, examination information is not necessarily supplied to the diagnostic reading request destination facility.

Moreover, although a case where the diagnostic reading report supplied from the diagnostic reading request intermediary device 2, or the like is displayed on the display unit with the monitor is described, the present invention is not limited thereto. For example, another output means such as a printer can be used.

Further, a part of the diagnostic reading request system 100 according to the embodiment or the diagnostic reading request intermediary device 2 can be implemented, for example, by using a computer as hardware. For example, with respect to the control unit 28 in the diagnostic reading request intermediary device 2 or the like, various kinds of functions can be implemented by causing a processor, such as a CPU, equipped on the abovementioned computer to execute a predetermined control program. In this case, in the diagnostic reading request intermediary device 2, the abovementioned control program can be installed on the computer in advance or stored in a memory medium readable by the computer, or a control program distributed via a network can be installed on the computer.

While certain embodiments have been described, these embodiments have been presented by way of example only, and are not intended to limit the scope of the invention. Indeed, the novel embodiments described herein may be embodied in a variety of other forms; furthermore, various omissions, substitutions and changes in the form of the embodiments described herein may be made without departing from the spirit of the invention. The accompanying claims and their equivalents are intended to cover such forms or modifications as would fall within the scope and spirit of the invention.

What is claimed is:

1. A diagnostic reading request system which requests diagnostic reading of clinical image data collected by a medical image diagnostic device to a diagnostic reading request destination facility connected thereto via a network, comprising:
   a computer processor configured to:
   create diagnostic reading request information by adding various kinds of identification information to the clinical image data;
   update the diagnostic reading request information by adding determination image data that is to be transmitted together with the clinical image data and has been associated with a reference diagnostic reading result;
   perform, based on a diagnostic reading result of the determination image data in the diagnostic reading request destination facility which is included in the diagnostic reading request information after update and the reference diagnostic reading result, an evaluation of the diagnostic reading result in the diagnostic reading request destination facility; and
   an output which outputs at least the evaluation of the diagnostic reading result;
   wherein updating the diagnostic reading request information includes extracting, from among various kinds of determination image data stored in advance with reference diagnostic reading results, the determination image data corresponding to the clinical image data, and
   adding the extracted determination image data to the diagnostic reading request information before update.

2. The diagnostic reading request system according to claim 1, the computer processor further configured to set virtual identification (ID) information, wherein the computer processor updates a part of the identification information included in the diagnostic reading request information before update to the set virtual identification information.

3. The diagnostic reading request system according to claim 2, wherein the computer processor sets the virtual identification (ID) information corresponding to at least any of a subject ID, a diagnostic reading request destination facility ID, and an image ID which are added to the clinical image data.

4. The diagnostic reading request system according to claim 1, computer processor further configured to extract, from among the various kinds of the determination image data, the determination image data having, as supplementary information, examination information that is the same or similar to examination information added to the clinical image data.

5. The diagnostic reading request system according to claim 1, the computer processor further configured to perform the evaluation of the diagnostic reading result in the diagnostic reading request destination facility by comparing at least any of the presence or absence of an abnormal part, a position of the abnormal part, a size of the abnormal part indicated by the reference diagnostic reading result of the determination image data with at least any of those indicated by the diagnostic reading result in the diagnostic reading request destination facility.

6. The diagnostic reading request system according to claim 1, the computer processor further configured to calculate a matching degree score indicating a matching degree between the diagnostic reading result in the diagnostic reading request destination facility and the reference diagnostic reading result using a calculation method set in advance, and perform the evaluation of the diagnostic reading result in the diagnostic reading request destination facility based on the matching degree score.

7. The diagnostic reading request system according to claim 1, further comprising an input, wherein the computer processor is further configured to perform the evaluation of the diagnostic reading result in the diagnostic reading request destination facility based on a diagnostic reading result evaluation request inputted in the input.

8. The diagnostic reading request system according to claim 1, the computer processor further configured to:
create a diagnostic reading report by adding any of diagnostic reading result evaluation ranking data and diagnostic reading result evaluation list data to the evaluation of the diagnostic reading result, the diagnostic reading result evaluation ranking data indicating, in an examination modality or in an examined organ, evaluations of diagnostic reading results in the diagnostic reading request destination facilities which are determined in previous diagnostic reading requests, the output outputs the diagnostic reading report.

9. A diagnostic reading request intermediary device which requests diagnostic reading of clinical image data supplied from a diagnostic reading request source medical facility to a diagnostic reading request destination facility connected thereto via a network, comprising:
a computer processor configured to
update diagnostic reading request information by adding determination image data that is to be transmitted together with the clinical image data and has been associated with a reference diagnostic reading result to the diagnostic reading request information in which various kinds of identification information are added to the clinical image data and which is supplied from the diagnostic reading request source medical facility;
perform, based on a diagnostic reading result of the determination image data in the diagnostic reading request destination facility which is included in the diagnostic reading request information after update and the reference diagnostic reading result, an evaluation of the diagnostic reading result in the diagnostic reading request destination facility; and
create a diagnostic reading report on the diagnostic reading request source medical facility based on at least the evaluation of the diagnostic reading result;
wherein updating the diagnostic reading request information includes extracting, from among various kinds of determination image data stored in advance with reference diagnostic reading results, the determination image data corresponding to the clinical image data, and
adding the extracted determination image data to the diagnostic reading request information before update.

10. A non-transitory computer readable medium including computer executable instructions which cause a diagnostic reading request intermediary device which requests diagnostic reading of clinical image data supplied from a diagnostic reading request source medical facility to a diagnostic reading request destination facility connected thereto via a network, to execute:
a request information update function of updating diagnostic reading request information by adding determination image data that is to be transmitted together with the clinical image data and has been associated with a reference diagnostic reading result to the diagnostic reading request information in which various kinds of identification information are added to the clinical image data and which is supplied from the diagnostic reading request source medical facility;
a diagnostic reading result evaluation function of performing, based on a diagnostic reading result of the determination image data in the diagnostic reading request destination facility which is included in the diagnostic reading request information after update and the reference diagnostic reading result, an evaluation of the diagnostic reading result in the diagnostic reading request destination facility; and
a diagnostic reading report creation function of creating a diagnostic reading report on the diagnostic reading request source medical facility based on at least the evaluation of the diagnostic reading result;
wherein the request information update function further includes extracting, from among various kinds of determination image data stored in advance with reference diagnostic reading results, the determination image data corresponding to the clinical image data, and
adding the extracted determination image data to the diagnostic reading request information before update.

11. A diagnostic reading result evaluation method, comprising:
selecting a diagnostic reading request destination facility, and creating a diagnostic reading result evaluation request including at least clinical image data collected by a medical image diagnostic device and identification information related thereto, in a diagnostic reading request source medical facility;
transmitting information about the selected diagnostic reading request destination facility; and the diagnostic reading result evaluation request from the diagnostic reading request source medical facility to a diagnostic reading request intermediary device;

updating the diagnostic reading request information by adding determination image data that is to be transmitted together with the clinical image data and has been associated with a reference diagnostic reading result to the diagnostic reading request information, by the diagnostic reading request intermediary device;

transmitting the diagnostic reading request information after update to the target diagnostic reading request destination facility, by the diagnostic reading request intermediary device;

receiving a diagnostic reading result of the determination image data in the diagnostic reading request destination facility which is included in the diagnostic reading request information after update and a diagnostic reading result of the clinical image data from the diagnostic reading request destination facility, by the diagnostic reading request intermediary device;

performing, based on the diagnostic reading result of the determination image data in the diagnostic reading request destination facility and the reference diagnostic reading result, an evaluation of the diagnostic reading result in the diagnostic reading request destination facility, by the diagnostic reading request intermediary device; and transmitting the diagnostic reading result of the clinical image data and the evaluation of the diagnostic reading result in the diagnostic reading request destination facility to the diagnostic reading request source medical facility, by the diagnostic reading request intermediary device;

wherein updating the diagnostic reading request information includes extracting, from among various kinds of determination image data stored in advance with reference diagnostic reading results, the determination image data corresponding to the clinical image data, and adding the extracted determination image data to the diagnostic reading request information before update.

12. The diagnostic reading result evaluation method according to claim 11, wherein updating the diagnostic reading request information in the diagnostic reading request intermediary device includes updating a part of the identification information to virtual identification information.

13. The diagnostic reading result evaluation method according to claim 11, wherein performing the evaluation of the diagnostic reading result in the diagnostic reading request destination facility, in the diagnostic reading request intermediary device, includes creating a diagnostic reading report on the diagnostic reading request source medical facility based on the evaluation of the diagnostic reading result.

14. The diagnostic reading result evaluation method according to claim 12, wherein performing the evaluation of the diagnostic reading result in the diagnostic reading request destination facility, in the diagnostic reading request intermediary device, includes creating a diagnostic reading report on the diagnostic reading request source medical facility based on the evaluation of the diagnostic reading result.

* * * * *